US010668013B2

(12) United States Patent
Seternes et al.

(10) Patent No.: US 10,668,013 B2
(45) Date of Patent: Jun. 2, 2020

(54) CHEWABLE GELLED EMULSIONS

(71) Applicant: VITUX GROUP AS, Oslo (NO)

(72) Inventors: Tore Seternes, Oslo (NO); Kurt Ingar Draget, Oslo (NO); Ingvild Johanne Haug, Oslo (NO)

(73) Assignee: VITUX GROUP AS, Oslo (NO)

( * ) Notice: Subject to any disclaimer, the term of this patent is extended or adjusted under 35 U.S.C. 154(b) by 0 days.

(21) Appl. No.: 15/639,047

(22) Filed: Jun. 30, 2017

(65) Prior Publication Data
US 2017/0296467 A1 Oct. 19, 2017

Related U.S. Application Data

(60) Continuation of application No. 14/515,297, filed on Oct. 15, 2014, now Pat. No. 9,724,296, which is a division of application No. 13/123,233, filed as application No. PCT/GB2009/002404 on Oct. 8, 2009, now abandoned.

(30) Foreign Application Priority Data

Oct. 8, 2009 (GB) .................................. 0818473.1

(51) Int. Cl.
| | |
|---|---|
| A61K 9/00 | (2006.01) |
| A61K 9/107 | (2006.01) |
| A61K 31/00 | (2006.01) |
| A61K 31/192 | (2006.01) |
| A61J 1/03 | (2006.01) |
| A61K 31/51 | (2006.01) |
| A61K 31/519 | (2006.01) |
| A61K 31/525 | (2006.01) |
| A61K 31/59 | (2006.01) |
| A61K 31/675 | (2006.01) |
| A61K 31/7135 | (2006.01) |
| A61K 31/714 | (2006.01) |
| A61K 33/10 | (2006.01) |
| A61K 47/10 | (2017.01) |
| A61K 47/14 | (2017.01) |
| A61K 47/20 | (2006.01) |
| A61K 47/22 | (2006.01) |
| A61K 47/36 | (2006.01) |
| A61K 47/42 | (2017.01) |
| A61K 45/06 | (2006.01) |
| A61K 47/26 | (2006.01) |

(52) U.S. Cl.
CPC ............. *A61K 9/0056* (2013.01); *A61J 1/035* (2013.01); *A61K 9/107* (2013.01); *A61K 31/00* (2013.01); *A61K 31/192* (2013.01); *A61K 31/51* (2013.01); *A61K 31/519* (2013.01); *A61K 31/525* (2013.01); *A61K 31/59* (2013.01); *A61K 31/675* (2013.01); *A61K 31/714* (2013.01); *A61K 31/7135* (2013.01); *A61K 33/10* (2013.01); *A61K 45/06* (2013.01); *A61K 47/10* (2013.01); *A61K 47/14* (2013.01); *A61K 47/20* (2013.01); *A61K 47/22* (2013.01); *A61K 47/26* (2013.01); *A61K 47/36* (2013.01); *A61K 47/42* (2013.01)

(58) Field of Classification Search
CPC ....... A61K 47/36; A61K 9/107; A61K 9/0056
See application file for complete search history.

(56) References Cited

U.S. PATENT DOCUMENTS

| | | | | |
|---|---|---|---|---|
| 3,873,720 | A | * | 3/1975 | Suzuki .................... A61K 31/23 514/547 |
| 4,428,927 | A | | 1/1984 | Ebert et al. |
| 4,695,450 | A | | 9/1987 | Bauer et al. |
| 4,764,383 | A | | 8/1988 | Brown et al. |
| 4,780,320 | A | | 10/1988 | Baker ........................... 424/493 |
| 4,935,243 | A | | 6/1990 | Borkan et al. |
| 4,961,939 | A | | 10/1990 | Antrim et al. .................. 426/61 |
| 5,004,611 | A | | 4/1991 | Leigh |
| 5,210,099 | A | | 5/1993 | Mody et al. ................... 514/557 |
| 5,258,184 | A | | 11/1993 | Bee et al. |
| 5,260,074 | A | | 11/1993 | Sipos |
| 5,300,302 | A | | 4/1994 | Tachon et al. |
| 5,549,204 | A | | 8/1996 | Toren ............................ 206/539 |
| 5,879,698 | A | | 3/1999 | Ellenbogen ............. A23L 1/303 424/440 |
| 6,253,920 | B1 | * | 7/2001 | Kallgren ............... B65D 75/327 206/532 |
| 7,652,068 | B2 | | 1/2010 | Feuerstein et al. |
| 2001/0036468 | A1 | | 11/2001 | Han et al. |
| 2003/0068407 | A1 | | 4/2003 | Chiavazza et al. |
| 2003/0099761 | A1 | | 5/2003 | Jost ........................ A23L 1/3056 426/656 |

(Continued)

FOREIGN PATENT DOCUMENTS

| | | |
|---|---|---|
| EP | 0 474 261 A2 | 3/1992 |
| EP | 0950402 A2 | 10/1999 |

(Continued)

OTHER PUBLICATIONS

Canadian Intellectual Property Office, "Notice of Allowance" dated Dec. 8, 2017, in Canadian Application No. 2,890,567 (based on UK Appln. 0818473.1).

(Continued)

*Primary Examiner* — Mark V Stevens
(74) *Attorney, Agent, or Firm* — IpHorgan Ltd.

(57) ABSTRACT

An oral pharmaceutical composition in unit dose form, each unit dose comprising a lipophilic drug substance within a unitary carrier body, said body comprising a soft, chewable, gelled oil-in-water emulsion.

9 Claims, 2 Drawing Sheets

(56) References Cited

U.S. PATENT DOCUMENTS

| | | | |
|---|---|---|---|
| 2003/0158265 A1 | 8/2003 | Radhakrishnan et al. | |
| 2003/0166670 A1 | 9/2003 | Brooks-Korn | 514/282 |
| 2004/0001873 A1 | 1/2004 | Base et al. | 424/439 |
| 2004/0018248 A1 | 1/2004 | Bendich | |
| 2004/0043043 A1 | 3/2004 | Schlyter et al. | |
| 2004/0058946 A1 | 3/2004 | Buchwald | |
| 2004/0121000 A1 | 6/2004 | Bowe et al. | |
| 2004/0248974 A1 | 12/2004 | Holmberg | 514/509 |
| 2005/0106233 A1* | 5/2005 | Andersen | A61K 9/4883 424/451 |
| 2005/0152968 A1 | 7/2005 | Brophy et al. | |
| 2005/0281748 A1 | 12/2005 | Hirsh et al. | |
| 2006/0034815 A1 | 2/2006 | Guzman | |
| 2006/0062810 A1 | 3/2006 | Woo et al. | |
| 2006/0088645 A1 | 4/2006 | Nietling et al. | |
| 2006/0165795 A1 | 7/2006 | Sawicka | 424/472 |
| 2006/0211763 A1 | 9/2006 | Fawzy | |
| 2006/0233873 A1 | 10/2006 | Meissonnier et al. | |
| 2007/0026075 A1 | 2/2007 | Shudo et al. | |
| 2007/0104741 A1 | 5/2007 | Murty et al. | |
| 2007/0128142 A1 | 6/2007 | Harrison et al. | 424/70.12 |
| 2007/0131342 A1 | 6/2007 | Buhrow et al. | 156/227 |
| 2007/0141138 A1 | 6/2007 | Feuerstein et al. | |
| 2007/0191467 A1 | 8/2007 | Rongen et al. | |
| 2007/0202049 A1 | 8/2007 | Guimberteau | |
| 2007/0213234 A1 | 9/2007 | Yaghmur et al. | 508/110 |
| 2007/0259957 A1 | 11/2007 | Ueshima et al. | |
| 2008/0008742 A1 | 1/2008 | Cherukuri | |
| 2008/0152595 A1 | 6/2008 | Emigh et al. | |
| 2008/0255247 A1 | 10/2008 | Sagalowicz et al. | 514/772 |
| 2008/0268042 A1 | 10/2008 | Feuerstein et al. | |
| 2009/0123386 A1 | 5/2009 | Young | |
| 2009/0130221 A1 | 5/2009 | Bolland et al. | |
| 2009/0196832 A1* | 8/2009 | Lakos | A61K 9/0056 424/43 |
| 2009/0220576 A1 | 9/2009 | Haug | |
| 2009/0238866 A1 | 9/2009 | Haug et al. | |
| 2009/0325895 A1 | 12/2009 | Wang et al. | 514/43 |
| 2010/0112047 A1 | 5/2010 | Feuerstein et al. | |
| 2010/0130611 A1 | 5/2010 | Feuerstein et al. | |
| 2010/0249045 A1 | 9/2010 | Babul | |
| 2011/0129442 A1 | 6/2011 | Magri' et al. | |
| 2011/0268770 A1 | 11/2011 | Seternes et al. | |
| 2011/0303573 A1 | 12/2011 | Feuerstein et al. | |
| 2013/0273025 A1 | 10/2013 | Draget | |
| 2013/0274280 A1 | 10/2013 | Draget | |

FOREIGN PATENT DOCUMENTS

| | | |
|---|---|---|
| EP | 1189620 B1 | 6/2004 |
| EP | 1782807 A1 | 5/2007 |
| EP | 1803440 | 7/2007 |
| EP | 1946755 A1 | 7/2008 |
| GB | 1474629 | 5/1977 |
| GB | 2 086 835 A | 5/1982 |
| JP | 1986277630 A | 12/1986 |
| JP | 5238954 A | 9/1993 |
| JP | 09-224578 | 9/1997 |
| JP | 11-056245 | 3/1999 |
| JP | 11-056315 | 3/1999 |
| JP | 2000-80027 | 3/2000 |
| JP | 2000-279107 | 10/2000 |
| JP | 2002524062 A | 8/2002 |
| JP | 2004-194514 A | 7/2004 |
| JP | 2004-520355 A | 7/2004 |
| JP | 2004-238419 A | 8/2004 |
| JP | 2005-500157 | 1/2005 |
| JP | 2005-512552 A | 5/2005 |
| JP | 2005527204 A | 9/2005 |
| JP | 2006-115831 A | 5/2006 |
| JP | 2007-500004 A | 1/2007 |
| JP | 2007-526269 A | 9/2007 |
| JP | 2009526760 A | 7/2009 |
| JP | 4943849 B2 | 5/2012 |
| WO | WO 96/09036 | 3/1996 |
| WO | 19960018387 A1 | 6/1996 |
| WO | 1999018967 A1 | 4/1999 |
| WO | 1999029316 A1 | 6/1999 |
| WO | WO 00/28973 | 5/2000 |
| WO | 2002024165 A2 | 3/2002 |
| WO | 2002043659 | 6/2002 |
| WO | WO 03/018186 A1 | 3/2003 |
| WO | WO 03/053159 A1 | 7/2003 |
| WO | 2004054539 A1 | 7/2004 |
| WO | WO 2004/054539 A1 | 7/2004 |
| WO | 2005-013714 A1 | 2/2005 |
| WO | 2005070399 A1 | 8/2005 |
| WO | 2005-084647 A1 | 9/2005 |
| WO | WO 2005/105290 A1 | 11/2005 |
| WO | 2005123039 A1 | 12/2005 |
| WO | 2006019140 A1 | 2/2006 |
| WO | WO 2006/021293 A1 | 3/2006 |
| WO | 2006065675 A2 | 6/2006 |
| WO | WO 2006/085675 A2 | 6/2006 |
| WO | 2006106344 A2 | 10/2006 |
| WO | WO 2007/018801 A1 | 2/2007 |
| WO | WO 2007060177 A1 | 5/2007 |
| WO | 2007085835 A1 | 8/2007 |
| WO | 2007085840 A1 | 8/2007 |
| WO | 20070085840 A1 | 8/2007 |
| WO | WO 2007085840 A1 * | 8/2007 ............ A23G 4/066 |
| WO | WO2007085840 A1 | 8/2007 |
| WO | 2008005318 A2 | 1/2008 |
| WO | WO 2008/005318 A2 | 1/2008 |
| WO | 2008045170 | 4/2008 |
| WO | 2008024490 A2 | 8/2008 |
| WO | 2006096806 | 9/2008 |
| WO | 2009053824 A1 | 4/2009 |
| WO | 2009095670 A1 | 8/2009 |
| WO | 2010041015 A2 | 4/2010 |
| WO | 2010041017 A2 | 4/2010 |
| WO | 2011128634 A2 | 10/2011 |

OTHER PUBLICATIONS

European Patent Office, "Intention to Grant" and "Decision to Grant", dated Feb. 16, 2017 and Nov. 6, 2017 respectively in European Application No. 15172196.6 (based on GB 0818473).

Indian Patent Office, "Hearing Notice" dispatched Dec. 7, 2017 in Indian Application No. 2640/DELNP/2011, based on PCT Application No. PCT/GB2009/002404 (with priority claim to UK 0818473. 1).

US Patent and Trademark Office, "Office Actions" dated Sep. 24, 2015 and Jun. 24, 2016 in parent U.S. Appl. No. 14/515,297.

European Patent Office, "Communication—Extended European Search Report" and related Annex, issued in counterpart European Application No. 15172196.6, dated Nov. 5, 2015 (7 pages).

Applicant submission to European Patent Office, "Request for Examination" and accompanying remarks, in counterpart European Application No. 15172196.6, dated May 27, 2016 (6 pages).

European Patent Office, "Communication under Rule 71(3)EPC—Intention to grant" and related Annex, issued in counterpart European Application No. 15172196.6, dated Sep. 21, 2016 (34 pages).

United States Patent and Trademark Office, "Notice of Allowance" and related documents dated Aug. 29, 2016 in U.S. Appl. No. 12/162,339.

United States Patent and Trademark Office, "Office Action" and "Notice of References Cited", dated Dec. 19, 2016 in U.S. Appl. No. 13/641,081.

Folador et al., "Fish meals, fish components, and fish protein hydrolysates as potential ingredients in pet foods", Journal of Animal Science 84(10):2752-2765 (2006).

United States Patent and Trademark Office, "Office Action" and "Notice of References Cited" dated May 18, 2016, and "Office Action" dated Nov. 15, 2016, in U.S. Appl. No. 13/641,084.

US Patent and Trademark Office, U.S. Appl. No. 12/162,339, Non-Final Office Actions dated Dec. 4, 2015; Mar. 12, 2014; and Jul. 20, 2011; Final Office Actions dated Dec. 22, 2014 and Feb. 16, 2012; and Restriction Requirement dated Jun. 2, 2011.

(56) References Cited

OTHER PUBLICATIONS

US Patent and Trademark Office, U.S. Appl. No. 13/641,081, Non-Final Office Actions dated Mar. 22, 2016 and Jul. 15, 2014; Final Office Action dated May 18, 2015; and Restriction Requirement dated Dec. 6, 2013.
US Patent and Trademark Office, U.S. Appl. No. 13/641,084, Non-Final Office Action dated Jul. 9, 2015; and Restriction Requirement dated Feb. 4, 2015.
European Patent Office, Examination, Communication Pursuant to article 94(3) EPC, European Application No. 11 715 601.8-1455, dated Feb. 11, 2014.
International Searching Authority, International Preliminary Report on Patentability, dated Oct. 16, 2012, European Patent Office, International Patent Application No. PCT/GB2011/000565, 2280 HV Rijswijk, The Netherlands.
European Patent Office, International Searching Authority, International Search Report, dated Mar. 21, 2012, European Patent Office, International Patent Application No. PCT/GB2011/000565, 2280 HV Rijswijk, The Netherlands.
UK Intellectual Property Office, Patents Act 1977: Search Report under Section 17(5), Intellectual Property Office, dated Aug. 23, 2010, Patents Directorate, Cardiff Road, Newport, South Wales, UK, Patent Application No. GB1006699.1.
European Patent Office, Acting as the International Search Authority,International Search Report and Written Opinion, PCT International Patent Application No. PCT/GB2011/000560, dated May 9, 2012.
United Kingdom Intellectual Property Office, Patents Act 1977: Search Report under Section 17(5), dated Aug. 25, 2010, Patents Directorate, Cardiff Road, Newport, South Wales, UK, Application No. GB1006200.8.
Kurt Ingar Draget, co-pending U.S. Appl. No. 13/641,091, 371(c) filing date of Jun. 4, 2013.
Hellio et al., "Physically and Chemically Crosslinked Gelatin Gels", Macromolecular Symposia 2006, vol. 241, pp. 23-27.
Japanese Patent Office, Office Action Decision of Rejection issued in Japanese Patent Application No. 2013-504328 dated Sep. 8, 2015.
Japanese Patent Office, Office Action issued in Japanese Patent Application No. 2013-504328, dated Jan. 6, 2015.
Eurasian Patent Office, Office Action issued in Eurasian Patent Application No. 201290985/28, dated Jan. 16, 2015.
Susan K. Raatz et al, Enhanced Absorption of n-3 Fatty Acids from Emulsified Compared with Encapsulated Fish Oil, Journal of the American Dietetic Association, Jun. 2009, 1076-1081, vol. 109 No. 6, Elsevier Inc., Iowa City, IA, USA.
James K. Roush et al, Multicenter Veterinary Practice Assessment of the effects of Omega-3 Fatty Acids on Osteoarthritis in Dogs, Journal of the American Veterinary Medical Association, Jan. 1, 2010, 59-66, vol. 236 No. 1, American Veterinary Medical Associaion, Schaumburg, IL, USA.
Pet Prescription website, http://petprescription.co.uk, Canikur Pro Paste, web page is archived and no longer available, Indexed on Sep. 18, 2010.
MSD Animal Health website, http://www.msd-animal-health.co.uk/Products_Public/Tryplase/Product_datasheet.aspx, Tryplase Capsules, web page is still active, copy was retrieved Jun. 17, 2013.
Rowena Dinham, Patents Act 1977: Search Report under Section 17(5), Intellectual Property Office, dated Aug. 20, 2010, Patents Directorate, Cardiff Road, Newport, South Wales, UK.
International Searching Authority, International Search Report and the Written Opinion of the International Searching Authority, European Patent Office, 2280 HV Rijswijk, The Netherlands.
Patent Office of Japan: Office Action dated Jul. 11, 2013 in counterpart Japanese Application No. 2011-530554.
Examination Report issued in counterpart European Application No. 09785201.6 dated Nov. 29, 2012 by the European Patent Office.
The UK Patent Office, "Search Report" issued in UK Application No. GB0818472.3 dated Feb. 6, 2009.
Yokoyama et al., "Effects of elcosaepentanoic acid on major coronary events . . . " Lancet 369:1090-1098 (2007).
Office Action and Notice of References Cited Issued by the US Patent & Trademark Office dated Oct. 9, 2012 and dated Jan. 29, 2013 in copending U.S. Appl. No. 13/123,163.
European Patent Office/International Searching Authority— "International Search Report" and "Written Opinion" dated Apr. 13, 2010 and "International Preliminary Report on Patentability" dated Apr. 12, 2011; all in PCT/GB2009/002406.
European Patent Office/International Searching Authority— "International Search Report" and "Written Opinion" dated Jul. 19, 2010 and "international Preliminary Report on Patentability" dated Apr. 12, 2011; all in PCT/GB2009/002404.
Search Report issued in UK Application No. GB 0818473.1 dated Feb. 5, 2009, serving as a priority document to the present application.
European Patent Office/International Search Authority, International Search Report and Written Opinion, PCT/GB2009/0085840, dated Jul. 19, 2010.
Tore Seternes et al, "Chewable Gelled Emulsions", U.S. Appl. No. 13/123,163, filed Apr. 7, 2011, national phase application of WO2010/0041017.

* cited by examiner

CHEWABLE GELLED EMULSIONS

CROSS-REFERENCE TO RELATED APPLICATIONS

This application is a continuing application of U.S. application Ser. No. 14/515,297, filed Oct. 15,2014, which is a continuing application of U.S. application Ser. No. 13/123,233, filed Apr. 7, 2011, which is the national stage completion application of PCT Application Number PCT/GB2009/002404, filed Oct. 8, 2009, which claims priority from Great Britain Application No. GB 0818473.1, filed Oct. 8, 2008. Each of these applications is incorporated by reference herein in its entirety.

This invention relates to oral pharmaceutical compositions comprising a soft, gelled oil-in-water emulsion containing a drug substance, preferably a lipophilic drug substance, but optionally a hydrophilic or amphiphilic drug substance, to processes for their preparation, and to their use.

Many drug substances, i.e. the physiologically active components of pharmaceutical compositions, are hydrophobic and as a result, when administered into the gastrointestinal tract, have poor uptake by the body. Besides being wasteful, this can mean that the patient has to take large or frequent doses, or that the drug substance has to be injected, a procedure that is more uncomfortable for the patient and that may require the cooperation of a doctor or nurse.

Moreover, when the unit dose of a drug substance is large, the oral unit dosage forms, e.g. tablets or capsules, may likewise be large and so difficult for elderly or young patients to swallow and moreover may cause a gagging reaction even with healthy adults. Accordingly, any therapeutic or prophylactic dosage regime which involves the consumption of large numbers of dose units or numbers of large, difficult to swallow, dose units is inherently at risk of patient non-compliance.

However, we have now found that lipophilic drug substances may be administered without these problems when contained within a piece of soft, chewable, gelled oil-in-water emulsion.

Moreover, we have found that the uptake of lipophilic compounds is increased by providing such compounds in the form of a soft, gelled oil-in-water emulsion.

Thus viewed from one aspect the invention provides an oral pharmaceutical composition in unit dose form, each unit dose comprising a lipophilic drug substance within a unitary carrier body, said body comprising a soft, chewable, gelled oil-in-water emulsion.

Viewed from a further aspect, the invention provides a process for preparing an oral pharmaceutical composition in unit dose form, which process comprises: forming an oil phase comprising a lipophilic drug substance dissolved or dispersed in a physiologically tolerable oil such as one comprising a polyunsaturated fatty acid ester, e.g. an omega-3 acid ester, an omega-6 acid ester, an omega-9 acid ester or a vegetable oil, preferably an omega-3 acid ester, particularly an EPA ester, a docosahexaenoic acid (DHA) ester or a combination of EPA and DHA esters; forming an aqueous phase comprising an aqueous solution of a physiologically tolerable gelling agent; forming an oil-in-water emulsion with said oil phase and said aqueous phase, allowing said emulsion to gel to form a soft chewable mass; and, before, during or after gelling of said emulsion, dividing said emulsion into dose units.

Viewed from a further aspect, the invention provides an oral pharmaceutical composition in unit dose form, each unit dose comprising a hydrophilic drug substance within a unitary carrier body, said body comprising a soft, chewable, gelled water-in-oil-in-water double emulsion. Here a water-in-oil emulsion comprising the water soluble drug substance in the aqueous phase is further emulsified with an aqueous phase comprising an aqueous solution of a physiologically tolerable gelling agent. This is especially useful when the hydrophilic drug substances to be administrated have a strong, unpleasant taste.

Viewed from a further aspect, the invention provides a process for preparing an oral pharmaceutical composition in unit dose form, which process comprises: forming an oil phase comprising a physiologically tolerable oil such as one comprising a polyunsaturated fatty acid ester, e.g. an omega-3 acid ester, an omega-6 acid ester, an omega-9 acid ester or a vegetable oil, preferably an omega-3 acid ester, particularly an EPA ester, a docosahexaenoic acid (DHA) ester or a combination of EPA and DHA esters; forming an aqueous phase comprising an aqueous solution of a hydrophilic drug substance dissolved or dispersed therein; forming a water-in-oil emulsion with said oil phase and said aqueous phase, forming an oil-in-water emulsion with said water-in-oil phase and a further aqueous phase, comprising an aqueous solution of a physiologically tolerable gelling agent, allowing said emulsion to gel to form a soft chewable mass; and, before, during or after gelling of said emulsion, dividing said emulsion into dose units.

The soft, gelled dose units of the present invention can remain intact during passage through the stomach and release the drug substances disposed within the gel matrix further down the gastrointestinal tract where the environment is not so harsh and where uptake is feasible. In this format some of the drug substance at the periphery of the matrix may be degraded by gastric fluid during stomach transit. Nonetheless, the soft, gelled dose units of the present invention have the advantage of being chewable and so more easily swallowed if large, e.g. above 1000 mg, more especially 1500 to 5000 mg. In the case where a large dose is required, the advantage of a single chewable dose unit may outweigh the relatively small loss of drug substance from the periphery of the chewed fragments during stomach transit. Chewable gel units moreover have the advantage that patient compliance is greater for patients with a gag reaction to swallowing tablets or capsules intact, in particular juvenile or elderly patients.

Thus viewed from one aspect the invention provides an oral pharmaceutical composition in unit dose form, each unit dose comprising a lipophilic drug substance within a unitary carrier body, said body comprising a soft, chewable, gelled oil-in-water emulsion capable of remaining substantially intact during passage through the stomach.

Thus viewed from one aspect the invention provides an oral pharmaceutical composition in unit dose form, each unit dose comprising a hydrophilic drug substance within a unitary carrier body, said body comprising a soft, chewable, gelled water-in-oil-in-water double emulsion capable of remaining substantially intact during passage through the stomach.

By soft and chewable it is meant that the gelled emulsion is readily deformable rather than rigid while yet being self supporting, i.e. that it will not flow like a viscous liquid, and that it may be readily fragmented upon chewing, i.e. so that it need not be swallowed whole. Typically, such a gelled emulsion may be compressed, at least substantially reversibly, i.e. elastically, by at least 10%, preferably at least 40% upon application of a force/deformation gradient of 0.1 mm/s at 21° C., 50% relative humidity and atmospheric pressure.

Preferably the compression breaking strengths of the soft, gelled dose units of the present invention are greater than 500 g/cm$^2$, particularly greater than 1000 g/cm$^2$, especially preferably greater than 2000 g/cm$^2$, e.g. 2900-3600 g/cm$^2$.

By unitary carrier body, it is meant that each dose unit contains one piece of gelled emulsion. Such pieces may be referred to hereinafter as "cores".

The cores may be formed from larger pieces of gelled emulsion, e.g. by cutting, or, more preferably by extrusion or molding of dose units of incompletely gelled emulsion.

By drug substance is meant a substance having a desirable therapeutic or prophylactic effect other than as a nutrient, i.e. substances of the type for which regulatory approval as a drug is required in for example the US or the European Union. Less preferably, the drug substance may be a vitamin which classifies as a drug substance for regulatory purposes, e.g. vitamin A, K or D (e.g. ergocalciferol, alphacalcidol and calcitriol). Vitamins, including these, as well as mineral and/or herbs may of course be included in the compositions in addition to non-vitamin drug substances.

By amphiphilic drug substance is meant a drug substance that will distribute at the oil droplet surface. In the single emulsion of the present invention the amphiphilic drug substance is mixed with the oil phase and in the double emulsion of the present invention the amphiphilic drug substance is mixed either with the oil or with the discontinuous aqueous phase of the double emulsion.

Examples of categories of suitable drug substances for use according to the invention include: analgesics; anti-inflammatories; anticancer agents; cardiovascular agents; biological agents; antiallergy agents (e.g. antihistamines); decongestants; antinausea agents, drugs affecting gastrointestinal function, drugs acting on the blood and blood-forming organs, drugs affecting renal and cardiovascular function, antifungal agents, urological agents, hormones, antimicrobial agents, antiepileptical agents, psycholeptical agents, antipsychotic agents, psychoanaleptical agents, anticholinesterase agents, drugs acting on the respiration organs and drugs acting on the eye.

Examples of particular lipophilic drug substances for use according to the invention include: temazepam; diphenhydramine; zolpidem; triazolam; nitrazepam; testosterone; estradiol; progesterone; benzodiazepines; barbiturates; cyclosporine; insulin; calcitonin; dextromethorphan; pseudoephedrine; phenylpropanolamine; bromocryptine; apomorphine; selegiline; amitriptyline; dextroamphetamine; phentermine; mazindol; compazine; chlorpromazine; perphenazine; fluoxetine, buspirone; clemastine; chlorpheniramine; dexochlorpheniramine; astemizole; loratadine; paracetamol; ketoprofen; naproxen; and, particularly, ibuprofen.

Examples of particular hydrophilic drug substances for use according to the invention include: sodium acetazolamide, acetyl salicylic acid, aminophylline, amiodarone hydrochloride, ascorbic acid, atenolol, bendroflumethiazide, calcium folinate, captopril, cetrizine hydrochloride, chloramphenicol sodium succinate, chlorpheniramine maleate, chlorpromazine hydrochloride, cimetidine hydrochloride, ciprofloxacin hydrochloride, clindamycin hydrochloride, clonidine hydrochloride, codeine phosphate, cyclizine hydrochloride, cyclophosphamide, sodium dexamethasone phosphate, sodium dicloxacillin, dicyclomide hydrochloride, diltiazem hydrochloride, diphenhydramine hydrochloride, disopyramide phosphate, doxepin hydrochloride, enalapril maleate, erythromycin ethylsuccinate, flecanide acetate, fluphenazine hydrochloride, folic acid, granisteron hydrochloride, guafenesin, haloperidol lactate, hydralazin hydrochloride, hydrochloroquine sulfate, hydromorphone hydrochloride, hydroxyzine hydrochloride, sodium indomethacin, isoniazid, isoprenaline hydrochloride, ketorolac trometamol, labetalol hydrochloride, lisinopril, lithium sulfate, mesoridazine benzylate, methadone hydrochloride, methylphenidate hydrochloride, methylprednisolone sodium succinate, metorprolol tartrate, metronidazole hydrochloride, metyldopa, mexiletine hydrochloride, molidone hydrochloride, morphine sulfate, naltrexone hydrochloride, neomycin sulfate, ondanstreon hydrochloride, orciprenaline sulfate, sodium oxacillin, oxybutynin chloride, oxycodone hydrochloride, paracetamol, penicillamine, pentoxifylline, petidine hydrochloride, sodium phenobarbital, potassium phenoxymethylpenicillin, phenylephrine hydrochloride, sodium phenytoin, potassium iodide, primaquine phosphate, procainamide hydrochloride, procarbazine hydrochloride, prochlorperazine maleate, promazine hydrochloride, promethazine hydrochloride, propranolol hydrochloride, pseudoephedrine hydrochloride, pyridostigmine bromide, pyridoxine hydrochloride, ranitidine hydrochloride, salbutamol sulfate, sodium ethacrynate, sotalol hydrochloride, sumatripan succinate, terbinafine hydrochloride, terbutaline sulfate, tetracycline hydrochloride, thioridazine hydrochloride, thiothixene hydrochloride, trifluoperazine hydrochloride, triprolidine hydrochloride, sodium valproate, vancomycin hydrochloride, vancomycin hydrochloride, verapamil hydrochloride, sodium warfarin.

The quantity of drug substance per unit dose of the compositions of the invention will conveniently be in the range of 50 to 200%, especially 80 to 120%, of the quantity per unit dose in conventional formulations of the drug substance or 25, 50 or 100% of the normal recommended daily adult or child dose. For ibuprofen, for example, the quantity per unit dose is preferably 100 to 1500 mg, especially 200 to 1200 mg, particularly 400 to 600 mg.

The compositions of the invention especially preferably consist of cores of gelled emulsion. However, less preferably, they may comprise a gelled emulsion core provided with a coating of a physiologically tolerable coating material. Such coatings may be of the type conventional within the pharmaceutical industry and may be applied by conventional means, e.g. spraying or dipping. For some applications, especially paediatric applications, a thin sugar (or otherwise sweetened) coating may be desired. Unless it is rapidly soluble in the mouth, however, rigid coatings are generally not desired since it is central to the invention that the soft gelled core be chewable so as to facilitate swallowing.

It is preferred that the cores be non-spherical as this facilitates chewing. While disc and lenticular forms are suitable, it is preferred that the cores be elongate, for example having cylindrical or similar form (optionally of course with rounded ends and one or more planar side faces). Where the application is paediatric, the cores may be in child-attractive forms, e.g. in a geometric shape or in the shape of an animal or cartoon character. In this way, the unit dose may be consumed with ease by patients who otherwise might have difficulty swallowing a conventional tablet or capsule, e.g. the young, the old, those with gag reactions, patients on chemotherapy, and others with reduced mouth function.

Since one major benefit of the compositions of the invention lies in their ease of consumption relative to conventional tablets or capsules, the cores will generally be quite large, e.g. having a mass of 100 to 3000 mg, especially 400 to 2000 mg, particularly 600 to 1500 mg. Where the drug substance dose per unit is quite small and the benefit of the invention lies in improved bioavailability, the cores may be smaller, e.g. as low as 50 mg, however even then larger cores may be used and in this event the compositions may be used as a source of beneficial oils, for example polyunsaturated fatty acid esters such as phospholipids, glycerides and lower alkyl (e.g. $C_{1-6}$ alkyl, especially ethyl) esters. Preferred polyunsaturated acids in this regard include the omega-3 acids, especially eicosapentaenoic acid (EPA) and docosahexaenoic acid (DHA).

The oil of the oil phase in the compositions of the invention may be any physiologically tolerable oil, such as one comprising a polyunsaturated fatty acid ester, e.g. an omega-3 acid ester, an omega-6 acid ester, an omega-9 acid ester or a vegetable oil, preferably an omega-3 acid ester, but will preferably be one or a mixture of fatty acid esters (for example phospholipids, mono-, di- or tri-glycerides, and lower alkyl esters). Such materials may be natural, synthetic or semi-synthetic. The use of plant and marine oils (e.g. oils from plant seeds, algae, fish (especially oily fish), microorgansims and marine invertebrates (especially krill)) is especially preferred as is the use of DHA and/or EPA ethyl esters. Mammalian oils will generally be undesired.

In one preferred embodiment, the oil of the oil phase may be a 90% mixture of ethyl EPA ester and ethyl DPA ester. This is available as Omacor® from Pronova Biocare AS, Lysaker, Norway.

Where the drug substance is not oxidation sensitive, it is generally preferred to use an oil which likewise is not oxidation sensitive since in this event the emulsion need not be guarded against oxidation during preparation or storage. Oils with low or no content of polyunsaturated acids may then be used. Where however the drug substance is oxidation sensitive, it may be preferred to use oils which are or majoritatively are polyunsaturated fatty acid esters, especially omega-3 esters, as these may function in part to reduce drug substance oxidation and as they may provide additional benefit to the consumer. Even where the drug substance is not oxidation sensitive, the use of oils which are or majoritatively are polyunsaturated fatty acid esters may be desirable, especially where such esters contribute to the beneficial effect of the drug, for example where the drug substance is a cardiovascular therapy or anticancer therapy agent.

Typically the oil phase will constitute 0.05 to 5 g, preferably 0.1 to 3 g, especially 0.2 to 2 g, particularly 0.3 to 1.25 g, more particularly 0.4 to 0.75 g, per dose unit. Alternatively put, the oil phase preferably constitutes 5 to 75% wt., especially at least 35 to 50% wt., e.g. 40 to 50% wt. of the dose unit.

The gelling agent used in the aqueous phase of the emulsion may be any physiologically tolerable gelling agent (preferably a saccharide (e.g. an oligosaccharide or polysaccharide), a protein or a glycoprotein) or combination capable of forming a soft, chewable, self-supporting gelled oil-in-water emulsion. Many such materials are known from the food and pharmaceutical industry and are discussed for example in *Handbook of hydrocolloids*, G O Phillips and P A Williams (Eds.), Woodhead Publishing, Cambridge, UK, 2000. The gelling agents are preferably materials capable of undergoing a sol-gel transformation, e.g. under the influence of a change in physiochemical parameters such as temperature, pH, presence of metal ions (e.g. group 1 or 2 metal ions), etc. Preferred gelling agents include gelatins, alginates and carrageenans. However, the use of gelatins is especially preferred as breakdown in the throat of trapped fragments is ensured and as cores having the desired properties may readily be produced using gelatins.

Here it should be emphasized that the gelled emulsion should be self-supporting, soft and fragmentable on chewing. It is not desired that the gelled emulsion should dissolve rapidly in the mouth without chewing as the administration of the composition would then differ little functionally from administration of an oil solution of the drug. Gelatin can be used to give the gelled emulsions these desired characteristics.

The gelatins used as gelling agents in the composition of the invention may be produced from the collagen of any mammal or the collagen of any aquatic species, however the use of gelatin from salt-water fish and in particular cold and warm water fishes is preferred.

Gelatins having an imino acid content of 5 to 25% wt. are preferred, more especially those having an imino acid content of 10 to 25% wt. The gelatins will typically have a weight average molecular weight in the range 10 to 250 kDa, preferably 75 to 220 kDa, especially 80 to 200 kDa. Gelatins having no Bloom value or low Bloom values of 60-300, especially 90-200 are preferred. Where a gelatin of no Bloom value, e.g. a cold water fish gelatin, is used, this will typically be used together with another gelatin or other gelling agent. The combination of cold water and warm water fish gelatins is especially preferred. The gelatin will typically be present in the aqueous phase at a concentration of 1 to 50% wt., preferably 2 to 35% wt., particularly 5 to 25% wt. In the case of mixtures of gelatin and polysaccharides, the weight ratio of gelatin to polysaccharide in the aqueous phase will typically be 50:1 to 5:1, preferably 40:1 to 9:1, especially 20:1 to 10:1.

Where polysaccharides, or mixtures of polysaccharides and gelatin are used as the gelling agent, it is preferred to use natural polysaccharides, synthetic polysaccharides or semi-synthetic polysaccharides, e.g. polysaccharides from plants, fish, terrestrial mammals, algae, bacteria and derivatives and fragmentation products thereof. Typical marine polysaccharides include carageenans, alginates, agars and chitosans. Typical plant polysaccharides include pectins. Typical microorganism polysaccharides include gellans and scleroglucans. The use of charged, e.g. electrostatically charged and/or sulfated polysaccharides is preferred, as is the use of marine polysaccharides, in particular carageenans, and alginates, especially carageenans. Carageenans are used below as representative polysaccharide gelling agents.

The carageenan family, which includes iota- and kappa-carageenans, is a family of linear sulfated polysaccharides produced from red algae. The repeating disaccharide unit in kappa-carrageenan is β-D-galactose-4-sulfate and 3,6-anhydro-α-D-galactose, while that in iota-carrageenan is β-D-galactose-4-sulfate and 3,6-anhydro-α-D-galactose-2-sulfate. Both kappa- and iota-carrageenans are used in food preparations. The carrageenans are used as stabilisers, emulsifiers, gelling agents and fat replacers.

Both iota and kappa carrageenans form salt- or cold-setting reversible gels in an aqueous environment. Coil-helix transition and aggregation of helices form the gel network. Kappa-carrageenan has binding sites for specific monovalent cations, resulting in gel formation with decreasing shear and elastic moduli in the order $Cs^+>K^+>>Na^+>Li^+$. As a rule, an increasing salt concentration enhances the elastic modulus and the setting and melting temperatures of a kappa-carrageenan gel. The use of water-soluble potassium, rubidium, or caesium compounds, particularly potassium compounds, and particularly naturally occurring compounds (e.g. salts) is preferred when kappa-carrageenan is used according to the invention, e.g. at concentrations of up to 100 mM, more especially up to 50 mM. A salt-dependent conformational transition is also found for iota-carrageenan. The molecules are also known to undergo coil-helix transition with strong helix-stabilisation in the presence of multivalent cations, like $Ca^{2+}$. The use of water-soluble calcium, strontium, barium, iron or aluminium compounds, especially calcium compounds, and particularly naturally occurring compounds (e.g. salts) is preferred when iota-carrageenan is used according to the invention, e.g. at concentrations of up to 100 mM.

The polysaccharide gelling agents used according to the invention will typically have weight average molecular weights of 5 kDa to 2 MDa, preferably 10 kDa to 1 MDa, most preferably 100 kDa to 900 kDa, particularly 200 to 800 kDa. They will typically be used at concentrations of 0.01 to 5% wt, preferably 0.1 to 1.5% wt., particularly 0.2 to 1% wt in the aqueous phase. Where mono or multivalent cations, typically group 1 or group 2 metal ions, are included in the aqueous phase, this will typically be at concentrations in the range 2.5 to 100 mM, particularly 5 to 50 mM.

Besides the gelling agent and water and any required gelling initiator, other physiologically tolerable materials may be present in the aqueous phase, e.g. emulsifiers, emulsion stabilizers, pH modifiers, viscosity modifiers, sweeteners, fillers, vitamins (e.g. vitamin C, thiamine, riboflavin, niacin, vitamin B6, vitamin B12, folacin, panthotenic acid), minerals, aromas, flavours, colours, physiologically active agents, etc. It is especially preferred that a lipophilic antioxidant, e.g. vitamin E, be included in the oil phase. Other vitamins which may be present in the oil phase are vitamin A, vitamin D and vitamin K. Such further components are used widely in the food, pharmaceutical and nutraceutical industries. The use of cellulose derivatives (e.g. hydroxy methyl propyl cellulose) as emulsion stabilizers is especially preferred.

The pH of the aqueous phase of the emulsion is preferably in the range 2 to 9, particularly 3 to 7.5.

The aqueous phase preferably has a gelling temperature in the range 10 to 30° C., more preferably 15 to 28° C., and a melting temperature in the range 20 to 80° C., more preferably 24 to 60° C., especially 28 to 50° C.

Where a sweetener is included in the aqueous phase, this will typically be selected from natural sweeteners such as sucrose, fructose, glucose, reduced glucose, maltose, xylitol, maltitol, sorbitol, mannitol, lactitol, isomalt, erythritol, polyglycitol, polyglucitol and glycerol and artificial sweeteners such as aspartame, acesulfame-K, neotame, saccharine, sucralose. The use of non-cariogenic sweeteners is preferred and the use of xylitol is especially preferred.

Where the drug substance is an analgesic, especially paracetamol or acetylsalicylic acid, or an antihistamine, it is preferred to use gelatin and/or to use an oil which is substantially free of polyunsaturated fatty acids, i.e. oxidatively stable.

Besides lipophilic drug substances, the gelled emulsion may be used as a delivery vehicle for calcium compounds, especially calcium carbonate, for use in the treatment or prophylaxis of osteoporosis. For this purpose, the calcium compound (e.g. a calcium salt (especially calcium carbonate) as described in WO00/28973 and WO96/09036, the contents of which are hereby incorporated by reference) may be dispersed in one or both of the oil and aqueous phases before or during gelation. Alternatively, a water or oil soluble calcium salt may be dissolved in the water or oil phase. In such compositions, it is especially desirable to include one or both of xylitol and vitamin D in the compositions, e.g. respectively in the water and oil phases.

Calcium tablets for osteoporosis treatment are typically large, crunchable discs weighing well over a gram so as to provide a calcium dose of about 500 mg. These tablets are extremely difficult to swallow whole and if crunched or allowed to dissolve release calcium carbonate particles into the mouth which may provide a long-lasting, unpleasant mouthfeel. Such tablets are required daily by the elderly and, since they are difficult to consume, there is a resulting problem with patient compliance. By presenting the calcium within a soft, chewable gelled oil-in-water emulsion of the type described herein, it is made much easier for the patient to consume the large daily dose, generally in two or a single dose unit.

The calcium compound present in the tablets preferably has a mean particle size by volume of 0.5-25 μm, especially 1-20 μm, particularly 2-15 μm.

Since tablet size is not an issue for the compositions of the invention, at least some of the calcium may be presented in dissolved form. (For solid, crunchable tablets, minimising tablet size to facilitate consumption has meant the presentation of the calcium as particulate calcium carbonate).

The daily calcium dose is preferably 500 to 2000 mg Ca, particularly 800 to 1500 mg Ca, especially about 1000 mg Ca. Where, as is preferred, vitamin D (e.g. vitamin $D_3$) is co-administered, the daily dose is preferably 100 to 1500 IU, particularly 200 to 1000 IU, especially 400 to 900 IU. A calcium to vitamin D ratio of 1 g Ca to 800-900 IU vitamin D is especially preferred. The proportion of this dose per dose unit of the composition of the invention is typically 20-100%, preferably about 25%, about 50% or about 100%, especially about 50% or 100%.

Thus viewed from a further aspect the invention provides an oral pharmaceutical composition in dose unit form comprising a physiologically tolerable calcium compound within a unitary carrier body, said body comprising a soft, chewable, gelled oil-in-water emulsion, and wherein the calcium content per dose unit is at least 125 mg Ca, for example 125 to 2000 mg Ca, especially 400 to 1200 mg Ca.

The dose units of the compositions of the invention may be formed in conventional fashion, e.g. preparation of the emulsion and formation of the emulsion into a gelled mass for example by dosing into molds before gelation is complete or by cutting a gelled mass into individual dose units, and, if desired, coating the gelled dose units. Emulsification and subsequent steps involving unpackaged gel are preferably effected under a non-oxidizing atmosphere, e.g. a nitrogen atmosphere.

Particularly preferably the dose units are blister packed and accordingly it is especially desirable to use the blistered layer of the blister packaging as the mold. The blister pack can then be foil sealed. The use of oxygen-impermeable foil packaging is especially preferred, e.g. as both laminate of a blister pack or as a single dose unit containing sachet. Oxygen-impermeable foils, e.g. metal/plastics laminates, are well known in the food and pharmaceuticals industries.

Viewed from a further aspect the invention provides the use of a drug substance for the manufacture of a composition according to the invention for use in a method of treatment of a human.

Viewed from a further aspect the invention provides a method of treatment of a human subject with an effective amount of a drug substance, said method comprising administering said substance to said subject orally in a composition according to the invention.

Viewed from a still further aspect the invention provides a pharmaceutical package, preferably a blister pack or sachet, comprising a foil-encased composition according to the invention.

Embodiments of the invention will now be described in the following non-limiting examples and the accompanying drawings, in which.

EXAMPLE 1

Drug-free Composition

Figure 1:
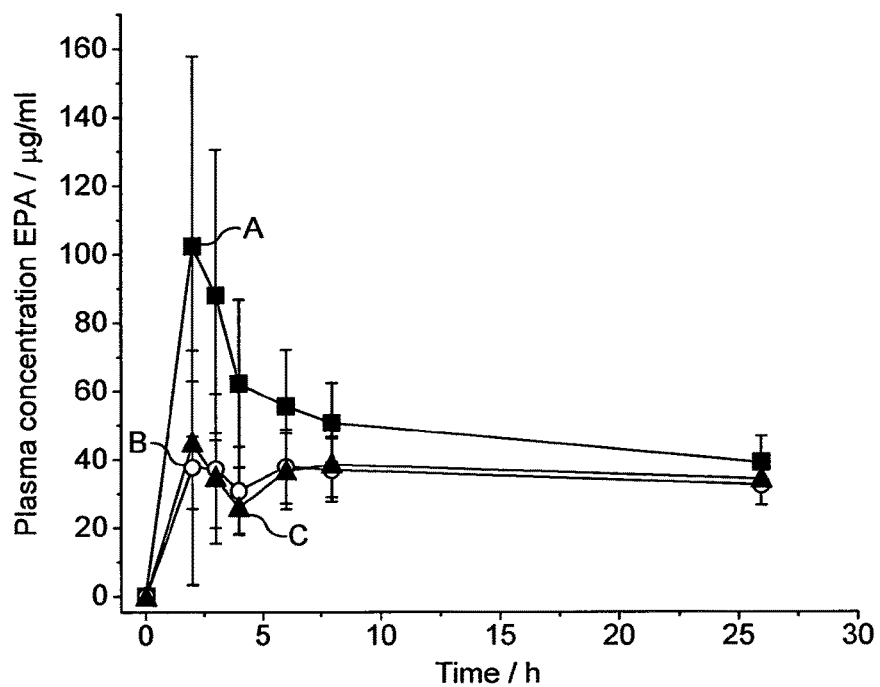
FIGS. 1 and 2 are graphs showing the omega-3 fatty acid concentration and composition of EPA and DHA respectively in total plasma delivered by three different administration forms.

An aqueous phase is formed from the following ingredients:

| | |
|---|---|
| Gelatin | 7.5% wt |
| Xylitol | 36% wt |
| Sorbitol | 14% wt |
| 50% Citric acid | 1% wt |
| Lemon flavour | 0.15% wt |
| Water | ad 100% wt |

Sunflower oil (or alternatively an omega-3 ester (Omacor®)) is emulsified with the aqueous phase in a weight ratio of 45:55 and the emulsion is poured in aliquots of 1.5 g into elongate moulds lined with a metal/plastics laminate blister tray and allowed to set. The blister tray is thermally sealed with a metal/plastics foil cover sheet.

EXAMPLE 2

Drug-containing Compositions

The drugs listed in Table 1 below are dissolved or dispersed in the oil or water phases used in Example 1 (in the oil phase if lipophilic or in the aqueous phase if not) at the concentrations per dose unit set out in Table 1 before emulsions are produced, poured and allowed to set as in Example 1. The set-gel dosage units are packaged as in Example 1.

For drug concentrations below 100 mg per dose unit, the dose units are conveniently 250, 500 or 750 mg. For concentrations above 100 mg per dose unit, the dose units are conveniently 500, 1000, 1500, 2000, 2500 or 3000 mg. Where an omega-3 ester is used as the oil of the oil phase, the dose units are preferably at least 1000 mg.

TABLE 1

| Drug substance | Dose per dose unit (mg) |
|---|---|
| Ibuprofen | 100-1500 (e.g. 200, 400, 600 and 800) |
| Naproxen | 250, 375 and 500 |
| Ketoprofen | 12.5-300 (e.g. 12.5, 50, 75, 100 and 200) |
| Paracetamol | 500-1000 |
| Loratadine | 10 |
| Astemizole | 10, 50 and 200 |
| Dexochlorpheniramine | 2-12 (e.g. 2, 4, 6 and 8) |
| Chlorpheniramine | 4 |
| Clemastine | 1 and 2 (as fumarate, 1.34 and 2.68) |

TABLE 1-continued

| Drug substance | Dose per dose unit (mg) |
|---|---|
| Diphenhydramine | 25 and 50 |
| Buspirone | 5, 10, 15, and 30 |
| Fluoxetine | 5-90 (e.g. 10 and 20) |
| Perphenazine | 2, 4, 8 and 16 |
| Chlorpromazine | 10, 25, 50, 100 and 200 |
| Prochlorperazine | 5, 10 and 15 |
| Mazindol | 1, 2 and 3 |
| Phentermine | 8-40 (e.g. 8, 15 and 30) |
| Dextroamphetamine | 5, 10 and 15 |
| Amitriptyline | 10, 25, 50, 75, 100 and 150 |
| Selegiline | 1.25, 5 and 10 |
| Apomorphine | 5 and 10 |
| Bromocryptine | 2.5 to 40 (e.g. 2.5, 5, 10, 15) |
| Phenylpropanolamine | 25, 50, 75, 400 and 600 |
| Pseudoephedrine | 60 and 120 |
| Dextromethorphan | 30-600 (e.g. 30, 90, 400) |
| Calcitonin | 5, 30, 35, 75 and 150 |
| Insulin | Recommended daily dose |
| Cyclosporine | 25 and 100 |
| Barbiturate (butabarbital) | 30, 50 and 100 |
| Benzodiazepine (e.g. temazepam, triazolam and nitrazepam) | 0.25, 0.5, 1 and 2 |
| Progesterone | 100, 200 and 300 |
| Estradiol (as estradiol valerinate) | 0.5, 1 and 2 |
| Testosterone (as testosterone undecanoate) | 10 |
| Nitrazepam | 0.3, 1, 2.5, 5 and 10 |
| Triazolam | 0.125, 0.25 and 0.5 |
| Zolpidem | 5 and 10 |
| Temazepam | 7.5, 15, 22.5 and 30 |
| Ergocalciferol | 10-200 kIU (e.g. 30000 IU) |
| Alphacalcidol | 0.25, 0.5, 1 and 2 micrograms |
| Calcitriol | 0.25, 0.5, 1 and 2 micrograms |

The selegiline, apomorphine, insulin and calcitonin dose units are preferably dissolved in the mouth rather than chewed/swallowed.

EXAMPLE 3

Gum Arabicum-containing Compositions

An aqueous phase is prepared using the following components:

| | |
|---|---|
| Gelatin | 5.7% wt |
| Xylitol | 24.2% wt |
| Sorbitol | 10.4% wt |
| 50% Citric acid | 0.6% wt |
| Lemon flavour | 1.1% wt |
| Gum arabicum | 3.7% wt |
| Water | ad 100% wt |

Drug-free and drug-containing dose units are prepared using this aqueous phase analogously to Examples 1 and 2.

EXAMPLE 4

Calcium Composition

An aqueous phase is prepared according to Example 1 but with an additional 1% wt hydroxypropyl methyl cellulose. 1250 mg/mL calcium carbonate (Scoralite 1B from Scora SA, France) is dispersed in this aqueous phase whereafter an emulsion is formed with the addition of cod liver oil (1:1 by volume) containing dissolved vitamin $D_3$. The emulsion is stirred until gelling begins whereafter it is dosed into moulds at a dose unit of 1250 mg CaCO₃ and 400 IU vitamin D₃ per dose unit. The dose units are sealed as in Example 1.

EXAMPLE 5

Randomised, Controlled Trial

The absorption of omega-3 fatty acids delivered by two different administration forms (two different formulations of omega-3 food supplements) is compared.

5 g omega-3 fatty acids (2.805 g eicosapentaenoic acid (EPA), 1.87 g docosahexaenoic acid (DHA)) in triglyceride form and 13 mg Vitamin E were administered to students of 18-28 years of age, in the form of either a soft gelled oil-in-water emulsion or as standard softgel capsules. Blood samples were collected after 0, 2, 3, 4, 6, 8 and 26 hours. The fatty acid concentration and composition in total plasma were measured.

In FIGS. 1-4, A and D correspond to administration of the soft-gelled oil-in-water emulsion of the present invention containing EPA or DHA respectively, B and E correspond to the administration of a standard omega-3 soft gel capsules containing a liquid marine phospholipid core and C and F correspond to the administration of standard omega-3 soft gel capsules containing a liquid triglyceride core.

Figure 2:
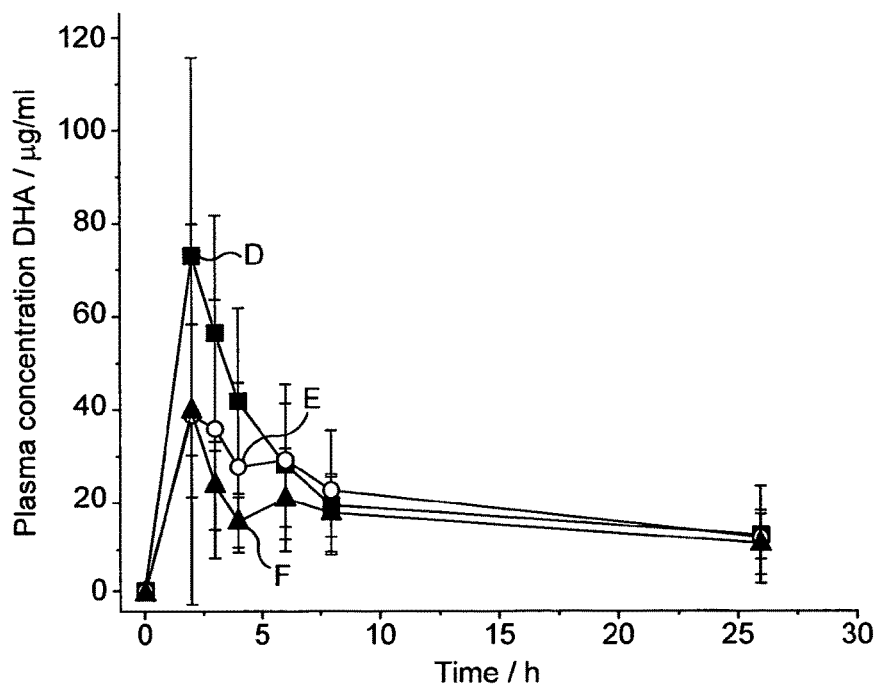

From FIGS. 1 and 2, it can be seen that lipophilic compounds (e.g. the omega-3 fatty acids EPA and DHA) are absorbed more quickly when administered in a soft gelled oil-in-water emulsion than when administered in the form of a standard soft gel capsule containing a liquid core.

Figure 3:
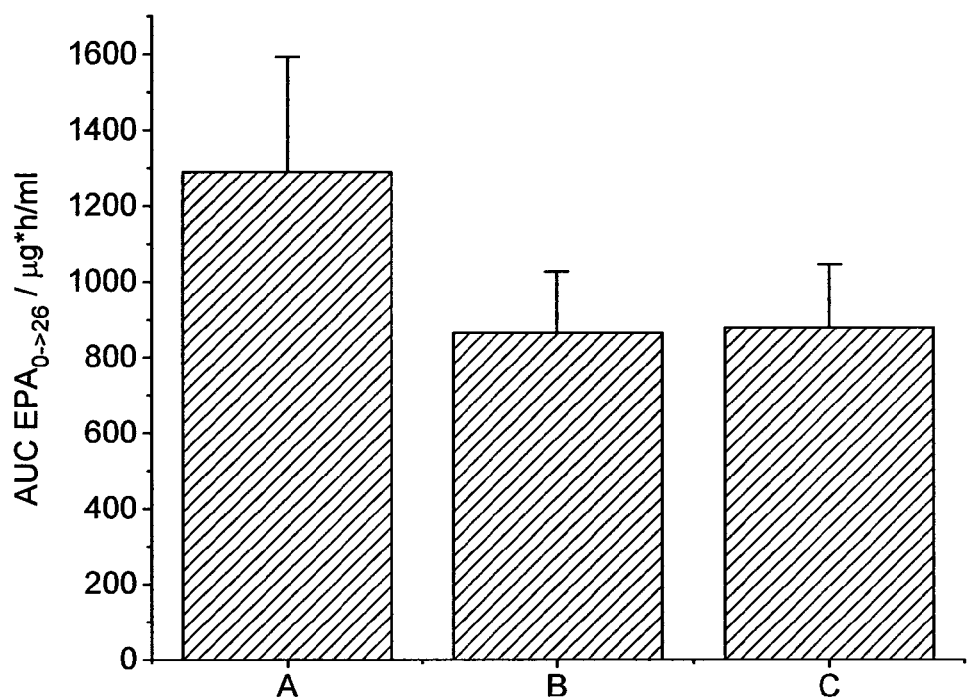
FIGS. 3 and 4 are graphs showing the total amount of EPA and DHA taken up respectively, i.e. the area under the curve of the graphs in FIGS. 1 and 2 respectively.
Figure 4:
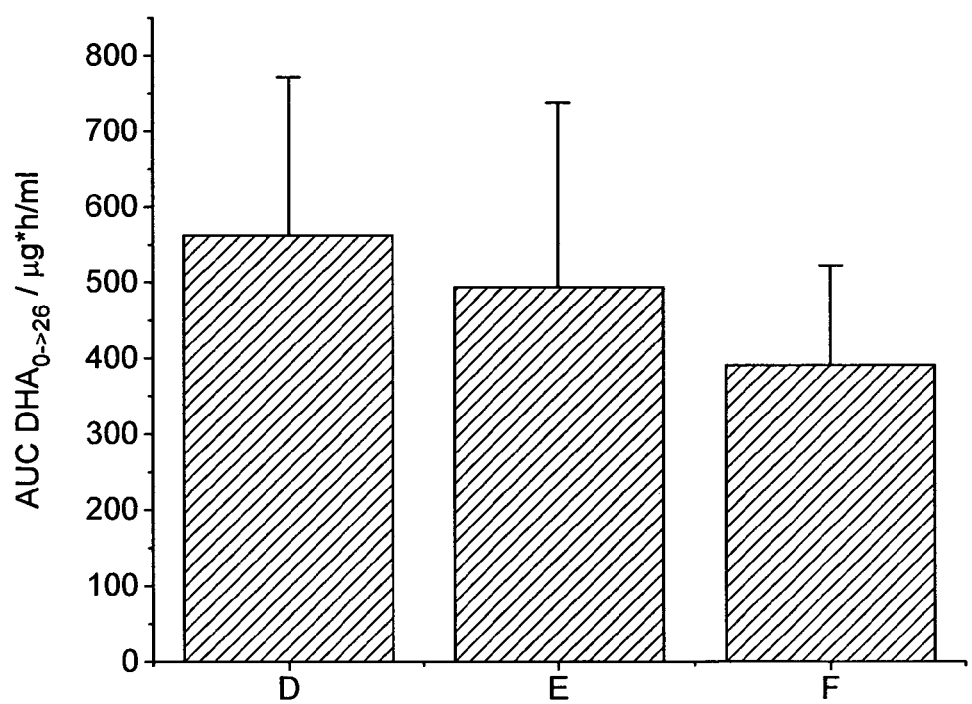

From FIGS. 3 and 4, it can be seen that a higher total plasma concentration of lipophilic compounds (e.g. the omega-3 fatty acids EPA and DHA) is achieved when administered in a soft gelled oil-in-water emulsion than when administered in the form of a standard soft gel capsule containing a liquid core.

EXAMPLE 6

Ibuprofen Composition (Double Emulsion)

An aqueous phase is formed from the following ingredients:

| Ibuprofen solution (50 (w/v)%) * | 71.6 wt % |
|---|---|
| Flavouring | 28.4 wt % |

* Solvent: 50 (v/v)% water 25 (v/v)% PEG (50 (w/v)%) 25 (v/v)% KOH (50 (w/v)%)

Sorbitan sesquiolate (or another emulsifier) is mixed with the oil (e.g. an omega-3 ester (Omacor®)) in a weight ratio of 5:95. This oil phase is emulsified with the aqueous phase in a weight ratio of 69:31 using an ULTRA-TURRAX® high-performance disperser (available from IKA).

A further aqueous phase is formed from the following ingredients:

| Gelatin | 17.2 wt % |
|---|---|
| Gum arabicum | 4.2 wt % |
| Sorbitol | 15.9 wt % |
| Xylitol | 29.6 wt % |
| Na-Saccharin | 0.1 wt % |
| Na-Cyclamate | 0.9 wt % |
| Citric acid | 0.9 wt % |
| Colouring | 1.5 wt % |
| Water | ad 100 wt % |

The above water-in-oil emulsion is further emulsified with the further aqueous phase in a weight ratio of 69:31 using an ULTRA-TURRAX® high-performance disperser and the water-in-oil-in-water emulsion (double emulsion) is poured in aliquots of 1.5 g into elongate moulds lined with a metal/plastics laminate blister tray and allowed to set. The blister tray is thermally sealed with a metal/plastics foil cover sheet.

EXAMPLE 7

Hydrophilic Drug-containing Compositions

The drugs listed in Table 2 below are dissolved or dispersed in the oil or water phases used in Example 6 at the concentrations per dose unit set out in Table 2 before emulsions are produced, poured and allowed to set as in Example 6. The set-gel dosage units are packaged as in Example 6.

TABLE 2

| Drug substance | Dose per dose unit (mg) |
|---|---|
| Acetazolamide sodium | 125 |
| Acetyl salicylic acid | 75 |
| Aminophylline | 100 |
| Amiodarone hydrochloride | 100 |
| Ascorbic acid | 25-100 |
| Atenolol | 25-100 |
| Bendroflumethiazide | 5-10 |
| Calcium folinate | 5-25 |
| Captopril | 12.5-100 |
| Cetrizine hydrochlorid | 2.5-10 |
| Chloramphenicol sodium succinate | 125 |
| Chlorpheniramine maleate | 2-12 |
| Chlorpromazine hydrochloride | 10-100 |
| Cimetidine hydrochloride | 100 |
| Ciprofloxacin hydrochloride | 100 |
| Clindamycin hydrochloride | 75-150 |
| Clonidine hydrochloride | 0.1-0.3 |
| Codeine phosphate | 15-60 |
| Cyclizine hydrochloride | 50-150 |
| Cyclophosphamide | 25-50 |
| Dexamethasone sodium phosphate | 0.25-6 |
| Dicloxacillin sodium | 125 |
| Dicyclomide hydrochloride | 20 |
| Diltiazem hydrochloride | 30-120 |
| Diphenhydramine hydrochloride | 12.5-50 |
| Disopyramide phosphate | 100 |
| Doxepin hydrochloride | 10-150 |
| Enalapril maleate | 2.5 |
| Erythromycin ethylsuccinate | 100 |
| Flecanide acetate | 50-150 |
| Fluphenazine hydrochloride | 1-10 |
| Folic acid | 0.4-1 |
| Graniteron hydrochloride | 1 |
| Guafenesin | 100 |
| Haloperidol lactate | 0.5-20 |
| Hydralazin hydrochloride | 10-100 |
| Hydrochloroquine sulfate | 200 |
| Hydromorphone hydrochloride | 1-8 |
| Hydroxyzine hydrochloride | 10-100 |
| Indomethacin sodium | 25-75 |
| Isoniazid | 50-100 |
| Isoprenaline hydrochloride | 10-15 |
| Ketorolac trometamol | 10 |
| Labetalol hydrochloride | 100 |
| Lisinopril | 2.5-40 |
| Lithium sulfate | 42-83 |
| Mesoridazine bensylate | 10-100 |
| Methadone hydrochloride | 5-40 |
| Methylphenidate hydrochloride | 5-20 |
| Methylprednisolone sodium succinate | 2-32 |
| Metorprolol tartrate | 50-100 |
| Metronidazole hydrochloride | 250 |
| Metyldopa | 125 |
| Mexiletine hydrochloride | 150 |
| Molidone hydrochloride | 5-100 |
| Morphine sulfate | 15-200 |
| Naltrexone hydrochloride | 50 |

TABLE 2-continued

| Drug substance | Dose per dose unit (mg) |
|---|---|
| Neomycin sulfate | 125 |
| Ondanstreon hydrochloride | 4-8 |
| Orciprenaline sulfate | 10-20 |
| Oxacillin sodium | 250 |
| Oxybutynin chloride | 5 |
| Oxycodone hydrochloride | 5-80 |
| Paracetamol | 80-160 |
| Penicillamine | 125 |
| Pentoxifylline | 400 |
| Petidine hydrochloride | 50-100 |
| Phenobarbital sodium | 15-100 |
| Phenoxymethylpenicillin potassium | 125 |
| Phenylephrine hydrochloride | 10 |
| Phenytoin sodium | 50-100 |
| Potassium iodide | 130 |
| Primaquine phosphate | 15 |
| Procainamide hydrochloride | 250 |
| Procarbazine hydrochloride | 50 |
| Prochlorperazine maleate | 5-30 |
| Promazine hydrochloride | 25-50 |
| Promethazine hydrochloride | 12.5-50 |
| Propranolol hydrochloride | 10-160 |
| Pseudoephedrine hydrochloride | 30-120 |
| Pyridostigmine bromide | 60-180 |
| Pyridoxine hydrochloride | 10-200 |
| Ranitidine hydrochloride | 75-150 |
| Salbutamol sulfate | 2-8 |
| Sodium ethacrynate | 25-50 |
| Sotalol hydrochloride | 80-160 |
| Sumatripan succinate | 25-50 |
| Terbinafine hydrochloride | 250 |
| Terbutaline sulfate | 2.5-5 |
| Tetracycline hydrochloride | 125 |
| Thioridazine hydrochloride | 10-150 |
| Thiothixene hydrochloride | 1-20 |
| Trifluoperazine hydrochloride | 1-10 |
| Triprolidine hydrochloride | 2.5 |
| Valproate sodium | 125 |
| Vancomycin hydrochloride | 125 |
| Verapamil hydrochloride | 40-120 |
| Warfarin sodium | 1-10 |

EXAMPLE 8

Vitamin B Composition (Double Emulsion)

An aqueous phase is formed from the following ingredients:

| Premix vitamin powder UF29278368 * | 11.8 wt % |
|---|---|
| Water | ad 100 wt % |

* Supplemix Multivit-Tab containing among others Vitamin B1 base, Vitamin B2, Vitamin B6 base, Vitamin B9 and Vitamin B12

Sorbitan sesquiolate (or another emulsifier) is mixed with the oil (e.g. caprilic/capric triglyceride (fractionated coconut oil)) in a weight ratio of 5:95. This oil phase is emulsified with the aqueous phase in a weight ratio of 50:50 using an ULTRA-TURRAX® high-performance disperser.

A further aqueous phase is formed from the following ingredients:

| Gelatin | 17.2 wt % |
|---|---|
| Gum arabicum | 4.2 wt % |
| Sorbitol | 15.9 wt % |
| Xylitol | 29.6 wt % |
| Na-Saccharin | 0.1 wt % |
| Na-Cyclamate | 0.9 wt % |
| Citric acid | 0.9 wt % |
| Colouring | 1.5 wt % |
| Water | ad 100 wt % |

The above water-in-oil emulsion is further emulsified with the further aqueous phase in a weight ratio of 69:31 using an ULTRA-TURRAX® high-performance disperser and the water-in-oil-in-water emulsion (double emulsion) is poured in aliquots of 1.5 g into elongate moulds lined with a metal/plastics laminate blister tray and allowed to set. The blister tray is thermally sealed with a metal/plastics foil cover sheet.

EXAMPLE 9

Calcium and Vitamin D Composition

An aqueous phase is prepared using the following components:

| Gelatin | 9.1% wt |
|---|---|
| Xylitol | 38.7% wt |
| Sorbitol | 16.6% wt |
| Citric acid | 0.9% wt |
| Gum arabicum | 5.9% wt |
| Water | ad 100% wt |

An oil phase is prepared using the following components:

| Flavouring | 25% wt |
|---|---|
| Vitamin D | 0.03% wt |
| Colouring | 5% wt |
| Sunflower oil* | ad 100% wt |

*or alternatively an omega-3 ester(Omacor ®)

The oil phase is emulsified with the aqueous phase in a weight ratio of 7:93. The emulsion is mixed with calcium carbonate powder (Eskal 500 from Staubtechnik, particle size 4-14 µm, ca. 80% by volume <10 µm) in a weight ratio of 1:1 to form a homogeneous solution and poured in aliquots of 1.5 g into elongate moulds lined with a metal/plastics laminate blister tray and allowed to set. The blister tray is thermally sealed with a metal/plastics foil cover sheet.

Analogous dose units, produced without Vitamin D, did not have the gritty or dustlike taste of other commercially available tablets. Instead, said dose units tasted like fizzy candy.

The invention claimed is:

1. An oral pharmaceutical composition in uncoated dose unit form comprising a physiologically tolerable calcium compound within a unitary carrier body, said body comprising a soft, chewable, gelled oil-in-water emulsion, wherein the calcium compound is dispersed in one or both of the oil and aqueous phases of the emulsion, and wherein the calcium content per dose unit is at least 125 mg Ca, and further wherein the aqueous phase comprises a gelling agent which is a physiologically tolerable polysaccharide and which is present at a concentration of 0.2 to 5% wt. in the aqueous phase, and the weight of the dose unit is 1000 mg to 5000 mg.

2. The composition as claimed in claim 1, containing particulate calcium carbonate.

3. The composition as claimed in claim 1, further containing xylitol.

4. The composition as claimed in claim 1, consisting of said gelled emulsion.

5. A pharmaceutical package comprising a composition as claimed in claim 1, wherein said composition is foil-encased.

6. The package as claimed in claim 5, in the form of a blister pack.

7. The composition as claimed in claim 1, wherein the physiologically tolerable polysaccharide is a carrageenan, an alginate, an agar, a chitosan, a pectin, a gellan or a scleroglucan.

8. The composition as claimed in claim 1, wherein the dose unit has a compression breaking strength of greater than 500 g/cm$^2$.

9. The composition as claimed in claim 1, wherein the gelled oil-in-water emulsion may be compressed at least substantially reversibly by at least 10% upon application of a force-deformation gradient of 0.1 mm/s at 21° C., 50% relative humidity and atmospheric pressure.

* * * * *